United States Patent [19]

Avalle

[11] Patent Number: 4,853,222

[45] Date of Patent: Aug. 1, 1989

[54] OINTMENT FOR CONCEALING SKIN BLEMISHES AND SCARS

[75] Inventor: Nadia Avalle, Lausanne, Switzerland

[73] Assignee: Intercos Italiana S.p.A., Italy

[21] Appl. No.: 76,351

[22] Filed: Jul. 22, 1987

[30] Foreign Application Priority Data

Aug. 1, 1986 [IT] Italy .................................. 21385 A/86

[51] Int. Cl.$^4$ .......................... A61K 7/035; A61K 9/06
[52] U.S. Cl. .................................... 424/195.1; 514/558
[58] Field of Search ........................ 424/195.1; 514/558

[56] References Cited

U.S. PATENT DOCUMENTS

| | | | |
|---|---|---|---|
| 3,911,105 | 10/1975 | Papantoniou et al. | 424/63 |
| 4,107,333 | 8/1978 | Hercelin et al. | 424/47 |
| 4,652,557 | 3/1987 | Sandborn | 514/164 |
| 4,707,293 | 11/1987 | Ferro | 424/70 |

*Primary Examiner*—William R. Dixon, Jr.
*Assistant Examiner*—E. McAvoy
*Attorney, Agent, or Firm*—Steele, Gould & Fried

[57] ABSTRACT

Ointment for concealing skin blemishes and scars comprising a greasy-waxy vehicle, a powder and additives, which contains from 0.1 to 4% of a synthetic wax or a hydrogenated castor oil and from 1 to 8% of octyl dodecanol.

10 Claims, No Drawings

OINTMENT FOR CONCEALING SKIN BLEMISHES AND SCARS

The present invention relates to an ointment for concealing skin blemishes and scars.

More precisely it relates to an ointment comprising a greasy-waxy vehicle, a powder and additives, which contains from 0.1 to 4% of a synthetic wax or a hydrogenated castor oil and from 1 to 8% of octyl dodecanol.

It is known that "satin finish foundations" are composed of triphasic systems comprising about 70% of water, 15 to 20% of a greasy-waxy vehicle and 10 to 15% of a powder.

After having been smeared on the skin and subsequent water evaporation, these preparations leave a thin layer consisting of approximately 50% waxes and grease and of a powder giving a light coverage (the remaining 50%).

These preparations are perfectly adequate to their function when applied to normal skins but their covering power is not sufficient at all when the skin is disfigured by pigmentation blemishes, bruising, redness, scars and by any surgical trauma or accidents.

A typical example of a field where the demand for concealing scars is high is the plastic surgery. In fact, even when the operation has been performed with great skill, a certain period has to elapse before the scar trauma is completely absorbed. In the absence of a preparation allowing complete coverage of the scars, the patient cannot resume his normal way of living until the scars disappear completely.

On the other hand, the scar concealing shows some specific and peculiar difficulties both due to the thinner and more sensitive epidermis of the scars which is therefore more prone to irritation and allergy and because it is smoother and still lacking in the complex epithelial structures promoting the adhesion of usual cosmetic preparations. Furthermore, the temperature of the scars is higher than that of the normal skin and therefore the perspiration is also higher.

For concealing skin blemishes in general and scars in particular, some preparations have been recently proposed containing approximately 50% of a greasy-waxy vehicle, whereas the remaining 50% consists of a powder.

Substantially it has been deemed that water elimination from usual "satin finish foundations" formulation would have resulted in a preparation that could have been smeared in thicker layers and would have hence produced a more efficient coverage and that, in the meantime would have been well tolerated like the traditional type "satin finish foundations".

On the contrary, when tested in practice these preparations have brought about a whole series of inconveniences. For instance, they show a very short "playing time"; in other words, their fluidity decreases very rapidly even before they can be spread evenly and in the desired manner. Besides that, they produce a thick and occlusive film unpleasant from both the aesthetical and functional point of view. In fact they block up the perspiration of the skin thus producing a situation of great discomfort and also possible negative side effects such as irritations.

Now, it has been surprisingly found that all these drawbacks are overcome by a preparation wherein the waxy portion comprises a synthetic wax or a hydrogenated castor oil and the greasy portion comprises octyl dodecanol.

In fact, it has been found that the addition of a waxy matter consisting of a synthetic wax or of a hydrogenated castor oil and of a greasy compound consisting of octyl dodecanol to an ointment which comprises from 20 to 40% of greasy-waxy vehicles, from 55 to 75% of a powder and from 1.2 to 3.1.% of additives, improves both the body and the structure of the ointment, and also the distribution degree of the powder as well as the "play time".

Once it has been spread on the skin, this ointment produces an adhesive, non occlusive, water-proof film having an excellent covering power and is less thick than that obtained by using known preparations for covering skin blemishes and scars.

The so obtained film does not hinder the normal perspiration of the skin, therefore it does not create a situation of discomfort and covers perfectly pigmentation defects, bruising, redness, scars and the like.

Furthermore, it is perfectly adherent also to the smooth skin of the scars, it is well tolerated, it does not give rise to irritations nor to allergies even near the eye, it stops sun rays therefore eliminating their irritating effect which is particularly pronounced when scars are involved; it does not have a pasty and unpleasant effect to the eye and it is not broken up or removed by water.

It can, however, be cleared away by a cleansing lotion.

On the film so obtained any conventional type make up can be applied as if it were usual satin finish foundation.

It is therefore an object of the present invention to provide an ointment for concealing skin blemishes and scars comprising a greasy-waxy vehicle, a powder and additives, which contains from 0.1 to 4% of a synthetic wax or hydrogenated castor oil and from 1 to 8% of octyl dodecanol.

Suitable types of synthetic waxes are the hydrocarbons prepared according to the Fisher-Tropsch method or by ethylene polymerization such as the product by the CAS number 8002-74-2.

A suitable type of hydrogenated caster oil is that obtained by controlled hydrogenation of castor oil such as that marked by the CAS number MX 8001-78-3.

In its turn the term octyl dodecanol is used to indicate 2-octyl dodecanol (CAS 5333-42-6).

As already indicated above, the amount of the greasy-waxy vehicle is preferably comprised from 20 to 40%, the powder percent is preferably from 55 to 75 and the additives are from 1.2 to 3.1.

Examples of suitable components of the greasy-waxy vehicle are cetyl alcohol, castor oil, lanolin and its derivatives, flowing vaseline, lecithin, hydrogenated oils, mineral oils, bees wax, rice wax, candelilla wax, carnauba wax, ozokerite, hard paraffin waxes, silicones, esters of vegetable hydrogenated resins, isopropyl miristate and mixtures thereof.

Examples of suitable components of the powder phase are talc, clay, silica, silica gel, titanium dioxide, iron oxides, bentonite, zinc oxide and mixtures thereof.

The additives may be of different types depending on the desired function; examples of suitable additives are the preservatives such as propyl para hydroxy benzoate, lubricants such as phenyl dimethicone, and anti-oxidants such as tocopherol, ascorbyl palmitate, citric acid, butyl hydroxy anisol, butyl hydroxy toluene and mixtures thereof.

The amount of preservatives will be preferably comprised from 0.1 to 0.3%, the anti-oxidants will also be comprised from 0.1 to 0.3% while the lubricants will preferably be comprised from 1 to 2.5%.

The ointment according to the present invention may be prepared according to known techniques.

Another object of the present invention is to provide a method for concealing the skin blemishes and scars, wherein the skin blemishes and scars are covered by an ointment according to this invention.

In the present description, as in the following examples, as well as in the claims, each time that reference is made to a part or to a percent, a part by weight and, respectively, a weight percent on the total weight is meant.

THe following examples are intended to illustrate this invention without, however, limiting it in any way.

EXAMPLE

| Components | Parts |
| --- | --- |
| 1. Vaseline oil | 9.80 |
| 2. Flowing vaseline | 16.00 |
| 3. Octyl dodecanol | 6.00 |
| 4. Ozokerite | 2.50 |
| 5. Phenyl dimethicone | 1.60 |
| 6. Hydrogenated triglyceride | 2.00 |
| 7. Synthetic resin C.A.S. 8002-74-2 | 0.50 |
| 8. Propyl para-hydroxybenzoate | 0.20 |
| 9. α-tocopherol/ascorbyl palmitate/citric acid/lecitin | 0.10 |
| 10. Talc | 8.00 |
| 11. Clay | 8.00 |
| 12. Silica | 0.30 |
| 13. Titanium dioxide | 41.30 |
| 14. Iron oxides | 4.00 |

The organic compounds from 1 to 9 were charged into a thermo-regulated plant equipped with a suitable homogenizing device and with an auxiliary apparatus for obtaining vacuum by suction. The temperature was set up at 85° C. until the waxy parts had softened.

Then the homogenizing device has been put into operation bringing the temperature up to 95° C. until a clear solution was obtained.

Compounds 13 and 14 were pre-mixed into a separate vessel with part of the above said organic phase. The so obtained mixture was refined by grinding and then charged into preceding plant containing the remainder of the organic phase. The so obtained mixture was homogenized at 95° C.; after about 40-60 minutes, compounds 10, 11 and 12 were added "as a veil" and the stirring continued for about additional 40 minutes, at the same temperature (95° C.).

Vacuum was made to deaerate perfectly the mixture; after about 20 minutes, the temperature was brought to 65° C. and the ointment was filtered through a large-size sieve (about 50 mesh).

An experiment was carried out with this ointment on nine individuals having skin blemishes (4 of them) and scars (5 of them). The ointment under test proved to be easily spreadable and to product an adhesive, non occlusive, water-proof film providing an excellent coverage.

Similar results have been obtained replacing a hydrogenated castor oil for the synthetic resin C.A.S. 8002-74-2 and adding different amounts thereof in the range from 0.1 to 4%.

Also addition of different amounts of octyl dodecanol in the range from 1 to 8% afforded similar results.

I claim:

1. An ointment for providing a film on the skin for concealing skin blemishes and scars comprising a greasy-waxy vehicle, a powder and additives, which contains from 0.1 to 4% of a synthetic wax or a hydrogenated castor oil and from 1 to 8% of octyl dodecanol.

2. An ointment according to claim 1, which comprises from 20 to 40% of greasy-waxy vehicles, from 55 and 75% of a powder and from 1.2.-3.1.% of additives.

3. An ointment according to claim 1, wherein the synthetic wax is marked by the CAS number 8002-74-2.

4. An ointment according to claim 1, wherein the hydrogenated castor oil is marked by the CAS number MX 8001-78-3.

5. An ointment according to claim 1, which contains from 0.1 to 0.3% of propyl para-hydroxybenzoate.

6. An ointment according to claim 1, which contains from 1 to 2.5.% of phenyl dimethicone.

7. An ointment according to claim 1, which contains from 0.1 to 0.3% of a compound selected from tocopherol, ascorbyl palmitate, citric acid or a mixture thereof.

8. An ointment according to claim 1, which contains 0.5% of the synthetic wax marked by the CAS number 8002-74-2.

9. An ointment according to claim 1, which contains 6% of octyl dodecanol.

10. A method of concealing skin blemishes and scars comprising covering the skin blemishes and scars with an ointment comprising a greasy-waxy vehicle, a powder and additives, which contains from 0.1 to 4% of a synthetic wax or a hydrogenated castor oil and from 1 to 8% of octyl dodecanol.

* * * * *